(12) United States Patent
Frondoza et al.

(10) Patent No.: US 6,886,568 B2
(45) Date of Patent: May 3, 2005

(54) METHOD FOR FABRICATING CELL-CONTAINING IMPLANTS

(75) Inventors: Carmelita G. Frondoza, Woodstock, MD (US); David J. Fink, Baltimore, MD (US); David S. Hungerford, Cockeysville, MD (US); Alan H. Shikani, Ruxton, MD (US)

(73) Assignees: The Johns Hopkins University, Baltimore, MD (US); Chrondros, Inc., Baltimore, MD (US)

( * ) Notice: Subject to any disclaimer, the term of this patent is extended or adjusted under 35 U.S.C. 154(b) by 155 days.

(21) Appl. No.: 09/825,632

(22) Filed: Apr. 4, 2001

(65) Prior Publication Data

US 2001/0014475 A1 Aug. 16, 2001

Related U.S. Application Data (63) Continuation-in-part of application No. 09/712,662, filed on Nov. 14, 2000, and a continuation-in-part of application No. 09/275,319, filed on Mar. 24, 1999, now Pat. No. 6,378,527.
(60) Provisional application No. 60/081,016, filed on Apr. 8, 1998, provisional application No. 60/104,842, filed on Oct. 20, 1998, and provisional application No. 60/165,608, filed on Nov. 15, 1999.

(51) Int. Cl.[7] ............................................. A61B 19/00
(52) U.S. Cl. ..................................... 128/898; 623/23.72
(58) Field of Search .......................... 128/898; 424/422; 623/13.17, 13.18, 23.72

(56) References Cited

U.S. PATENT DOCUMENTS

| | | | | |
|---|---|---|---|---|
| 5,496,722 A | * | 3/1996 | Goodwin et al. | 435/371 |
| 5,618,531 A | * | 4/1997 | Cherksey | 424/93.7 |
| 5,965,125 A | * | 10/1999 | Mineau-Hanschke | 424/93.21 |

FOREIGN PATENT DOCUMENTS

| | | | | |
|---|---|---|---|---|
| JP | 61216679 A | * | 9/1986 | C12M/1/02 |

* cited by examiner

*Primary Examiner*—Corrine McDermott
*Assistant Examiner*—Thomas Barrett
(74) *Attorney, Agent, or Firm*—Armstrong, Kratz, Quintos, Hanson & Brooks, LLP (57) ABSTRACT

Disclosed is a method of growing cells on biodegradable microcarrier particles and more specifically growing chondrocytes for an extended period of time until they aggregate. These aggregated cells can be injected directly or shaped for implantation into the body. In another embodiment of this invention, the cell microcarrier aggregates are grown in a mold that is shaped to conform to the geometry of the desired body part to be replaced. An apparatus for shaping the aggregated cells is disclosed. The aggregated cells can be supplied in a kit.

34 Claims, 6 Drawing Sheets

FIG. 7

METHOD FOR FABRICATING CELL-CONTAINING IMPLANTS

RELATED APPLICATIONS

This application is related to provisional applications Ser. No. 60/081,016 filed Apr. 8, 1998 and Ser. No. 60/104,842 filed Oct. 20, 1998 and is a continuation-in-part of Ser. No. 09/275,319 filed Mar. 24, 1999 now U.S. Pat. No. 6,378,527, and is also related to provisional application Ser. No. 60/165,608, filed Nov. 15, 1999, and is also a continuation-in-part of Ser. No. 09/712,662, filed Nov. 14, 2000.

FIELD OF THE INVENTION

The herein disclosed invention finds applicability in the field of cell culture, as well as in the field of preparing tissue substitutes for tissue replacement and for prosthesis.

BACKGROUND

Attempts at replacing or rebuilding diseased or damaged structures in the human body go back to 3000 B.C. It was not until the middle of the 1900's, however, that the use of synthetic materials for rebuilding body structures met with widespread and reproducible success. Advances in material science and biomaterials have afforded much of the success. The need for new and better implants exists in every field of medicine in which disease or trauma can be treated surgically.

As technology continues to improve the state of the art, the standards for successful implants continue to improve performance factors such as mechanical properties, bioresorption, biocompatibility and integration into existing tissues. The new research being conducted today on growth factors and cytokines, controlled drug release, and cell-based therapies anticipate a time when implant materials will be expected to promote healing, alter disease process and stimulate tissue regeneration.

The inventors have continued to make improvements to produce good quality cartilage cells in sufficient quantity to be transplanted effectively. The inventors have previously described a microcarrier spinner culture system that facilitated maintenance of chondrocytic phenotype while enhancing proliferation. The chondrocytic phenotype is characterized by expression of collagen type II and a family of high molecular weight, aggregating, sulfate-containing proteoglycans known as aggrecan. This culture system was based on a bioreactor originally designed to grow bacteria in large quantities. Articular and nasal septal chondrocytes have been grown on dextran or Cellagen™ (highly cross linked collagen type I) microcarrier beads under controlled pH, oxygen levels, nutrient supply and mechanical agitation conditions. Under these conditions, fibroblastic chondrocytes, which were originally propagated in traditional monolayer culture began to re-express their chondrocytic phenotype while propagating to 20 times their original number. This represents a great advantage over the traditional static monolayer culture system, which facilitates proliferation but leads to a fibroblastic shift in phenotype. Likewise, it offers an alternative to the battery of three-dimensional gel or scaffold systems, which include agarose or collagen gels, calcium alginate gel, mixed fibrin-alginate gels, three-dimensional meshes of resorbable polymers such as polylactide, and encapsulation in alginate beads. These culture techniques facilitate the maintenance of a chondrocytic phenotype, but are limited in maximizing proliferation.

The inventors have also utilized nasal cartilage as a source of chondrocytes. Like articular cartilage, nasal cartilage is hyaline cartilage, and the chondrocyte is its only cellular component. Nasal cartilage is also readily obtained from nasal septal surgery. The tissue offers a source of normal chondrocytes and provides an alternative model to using chondrocytes of nonhuman origin, immortalized cell lines or human osteoarthritic cartilage, which may not accurately represent normal human chondrocytes.

Improvements of the invention are set forth below and the subject matter of Ser. No. 09/275,319 filed Mar. 24, 1999 and Ser. No. 09/712,662, filed Nov. 14, 2000 are incorporated by reference herein in their entirety.

SUMMARY OF THE INVENTION

The herein disclosed invention can be described as a method of preparing cells for implantation comprising allowing cells (e.g., chondrocytes) to grow on microcarrier particles for an extended period of time and to secrete extracellular matrix components, thereby, producing a cell-microcarrier aggregate useful for implantation to a patient. The cell-microcarrier aggregates can be implanted directly or further cultured inside a mold that has been shaped to configure the geometry of the area of the body receiving the cells for implantation. When further cultured in a mold, cell-microcarrier aggregates are consolidated into an inplantable structure for repair or replacement of missing or diseased tissue. The microcarrier used to prepare the aggregate is a biocompatible, biodegradable material. Culturing of said cells and microcarriers takes place over a period of one to five weeks. The cells are seeded onto the microcarrier at a density of 1 to $4 \times 10^3$ cells/cm$^3$. This method also anticipates that cell-microcarrier aggregates, or consolidated implants prepared therefrom by further culturing in a mold, may be cryopreserved by standard methods in order to maintain cell viability and aggregate structure for future implantation or analysis.

One embodiment of the method of the invention involves replacing a tissue or body part or filling a void in head and neck area comprising the steps of obtaining a non-diseased, cell sample from the respective patient's head and neck area, rapidly growing additional cells in a bioreactor and within a predetermined mold which is the mirror image of the patient's tissue, body part or void, such that a molded tissue or body part is produced, and surgically implanting the molded tissue or body part as a replacement in the patient's head and neck area, such that the molded tissue or body part regenerates therein and thereby may integrate with the adjacent tissues in the head and neck area of the respective patient. In a more general embodiment of the invention, cells may be obtained from any anatomic location of the patient to receive the implant or from another donor human, and the resulting material produced by the method may be implanted at any location requiring the implant.

In another embodiment of the invention, cell-microcarrier aggregates are cultured to provide a suspension of individual aggregates that may be implanted by injection by syringe or by other endoscopic or arthroscopic instruments suitable for their implantation into a diseased or damaged anatomic site. In this embodiment, cell-microcarrier aggregates may be implanted without any additional material to bind the aggregates together after implantation. Alternatively, a material capable of polymerizing or gelling after implantation may be mixed with the aggregate suspension prior to implantation in order to improve the fixation and localization of the aggregates after implantation, to stimulate more rapid consolidation of the aggregates in vivo, or to promote more rapid integration of the aggregates into the surrounding tissue.

Contemplated by this invention is an "implant assembly unit" (IAU) comprising a mold arrangement to be used with a spinner-culture apparatus, said mold arrangement having a top lid and a bottom chamber defining a molding compartment therebetween and wherein said molding compartment has an inlet and outlet to allow culture media to flow therethrough and allowing consolidation of the cell-microcarrier aggregates into the shape desired for implantation. The top lid and bottom chamber may be separated to remove the formed implant material. Alternatively, the IAU may be an integral part of the spinner culture system, thereby allowing formed cell-microcarrier aggregates to be collected in the IAU, and cultured to consolidate them into a desired shape, without removing them from the spinner culture system.

Also contemplated in this invention is a kit comprising the implant material and a means for implanting the implant into the desired anatomic site. For example, the kit may comprise a fluid suspension of cell-microcarrier aggregates and a syringe or arthroscopic or endoscopic device to be used for injecting the suspension into the desired anatomic site. Alternatively, the kit may comprise a molded implant formed by further culturing the cell-microcarrier aggregates to form a solid device, tools for further shaping the implant intraoperatively, and tools or materials for implanting the implant by open or minimally invasive surgical procedures.

A method is disclosed for fabricating implants for use in repairing or reconstructing missing or diseased tissues. This method is based on the observation that chondrocytes, seeded onto microcarriers and culture expanded in suspended (spinner) culture, secrete extracellular matrix components into their pericellular spaces and eventually begin to aggregate into cartilage-like structures that can serve as implant devices for surgical repair of cartilaginous tissues. The method includes the following steps: (1) isolating the cells to be implanted from donor tissue; (2) seeding the cells onto resorbable microcarriers or beads; (3) culturing the cells on the microcarriers or beads to achieve an expansion in the number of cells; (4) concentrating and transferring the cell-containing microcarriers to a device called "implant assembly unit" (IAU) having the geometry desired for implantation; (5) further culturing the microcarriers seeded with cells in the designed IAU until the formation of a consolidated construct of the desired geometry and properties is achieved. This method results in the formation of an in-vitro cultured implant without the need for a preformed scaffold onto which the cells are initially seeded. Moreover the method can be conducted in a "closed" system following introduction of the isolated donor cells and microcarrier.

Alternatively, the culture-expansion step (Step 3) may be conducted directly in an appropriately designed IAU that is an integral part of the spinner culture system, thereby negating the need for the transfer in Step 4.

In another embodiment of the invention, the suspension of chondrocytes culture-expanded on microcarrier beads (Step 3) may be harvested prior to the formation of consolidated aggregates. This suspension may then be used as an injectable implant that will conform to the anatomic space requiring augmentation or repair, wherein extracellular matrix secretion continues and the cell-microcarrier construct forms a consolidated aggregate in situ.

Prior Art Patents

Goodwin (U.S. Pat. No. 5,496,722) teaches a method of producing non-neoplastic three dimensional mammalian tissue and cell aggregates under microgravity culture conditions. The product and method of the herein disclosed invention is distinct from that of Goodwin. Since Goodwin employs microgravity, or culture conditions that reproduce the effects of microgravity in which there is no relative movement of the fluid and suspended cell-microcarrier aggregates. Under these conditions, interaction between aggregates is minimized. In the herein disclosed invention spinner-culture under normal gravity conditions is used, where there is agitation of the fluid allowing aggregate—aggregate contact, and thereby the instant inventions are able to aggregate a sample of much larger size. Note that Goodwin after 1000 hours of culture obtained a chondrocyte aggregate of 0.4 cm in length while the aggregates of the herein disclosed invention aggregate to sizes in the range of from 0.1 to 4 cm. Note also that the instant invention uses spinner culture which will deliver a larger aggregate because the aggregate is in spin-culture suspension, while Goodwin's microgravity culture is unable to keep the cell aggregates in suspension to produce bumping contact of the cells on the carrier and, thus, form an enlarged aggregate. Goodwin, because his process is carried out under microgravity conditions, does not produce sufficient contact between aggregates to produce adequate aggregate size or to allow the cell-microcarrier aggregates to consolidate into larger agglomerate structures. The herein disclosed invention produces aggregates of adequate size.

Caplan et al in the U.S. Pat. No. 5,855,619 disclose an implant for repair of tissue which has been prepared by culturing cells in an open-ended cylindrical device. Culture takes place for approximately twenty hours. In the process described in the instant invention the chondrocytes are cultured for a much longer period of time.

Caplan et al in the U.S. Pat. No. 5,197,985 disclose a method and device for enhancing the implantation and differentiation of marrow-derived mesenchymal cells for treating skeletal and other connective tissue disorders. Cells are cultured in porous calcium phosphate carriers for 90 minutes to promote attachment of the cells to the interior of the carrier.

Caplan et al in the U.S. Pat. No. 5,226,914 further disclose methods for repair of tissue which has been prepared by culturing cells in an open-ended cylindrical device made of porous calcium phosphate. Culture takes place for 90 minutes prior to implantation.

Griffith-Cima et al in the U.S. Pat. No. 5,709,854 disclose methods for implanting cell into animals wherein a cell-polymer solution is injected into the animal and wherein the polymer crosslinks in situ to form a polymeric hydrogel containing dispersed cells which subsequently form new tissue. Crosslinking of the polymer results from using cations or anions, altering the pH or changing the temperature.

Nevo et al in the U.S. Pat. No. 4,642,120 disclose the use of embryonal chondrocytes, or any other kind of mesenchyme originated cells which can be converted in vitro or in vivo to cartilage cells by the influence of chondrogenic inducing factors, in a suitable biological milieu, which forms a "gel". The cells are contained in the gel carrier, without culturing in vitro, and used for repair of articular cartilage defects.

Grande in the U.S. Pat. No. 4,846,835 discloses a grafting technique wherein chondrocytes, preferably seeded in a three-dimensional collagen matrix, are used for promoting the healing of lesions in articular cartilage, wherein a periosteal flap is used to internally fix the graft during the healing process. The chondrocytes can be either implanted immediately after seeding of the collagen matrix, or the cell-matrix combination may be cultured for 2–3 days prior to implantation.

Itay in the U.S. Pat. No. 4,904,259 discloses methods for repair of cartilage or bone defects using cells expressing a chondrocyte phenotype embedded in a biocompatible matrix containing about 20% serum. The cells are embedded in the matrix and directly implanted, or the cell-matrix combination may be cryopreserved prior to implantation.

Vacanti et al in U.S. Pat. No. 5,041,138 disclose methods and artificial matrices for the growth and implantation of cartilaginous structures and surfaces. In the preferred embodiments, chondrocytes are grown on biodegradable, biocompatible fibrous polymeric matrices for extended periods up to 28 days prior to implantation. Methods for molding or shaping fibrous matrices to form desired anatomic shapes such as ears or noses is taught.

Vacanti et al in the U.S. Pat. No. 5,736,372 disclose additional methods and artificial matrices for the growth and implantation of cartilaginous structures and surfaces and bone.

Vibe-Hansen et al in the U.S. Pat. No. 5,759,190 disclose methods for the treatment of articulating joint surface cartilage by the transplantation of chondrocytes in a suitable matrix, in the presence of a hemostatic barrier and a covering-patch.

Tubo et al in the U.S. Pat. No. 5,786,217 disclose methods and compositions for the repair of articular cartilage defects wherein denuded chondrogenic cells are proliferated ex vivo as monolayer cultures in order to expand the pool of available chondrogenic cells, but whereby the chondrogenic cells stop secreting the extracellular matrix typical of cartilage.

Uniqueness of the Herein Disclosed Invention

This invention describes a process for fabricating implants for use in repairing or reconstructing missing or diseased tissues.

The method of the invention includes the following steps:
1. isolating the cells to be implanted from donor tissue;
2. seeding the cells onto a biodegradable microcarrier or bead (the terms microcarrier and bead are used interchangeably herein);
3. culturing the cells on the microcarriers to achieve an expansion in the number of cells;
4. concentrating the cell-containing microcarriers in a designed culture chamber having the geometry desired for implantation;
5. further culturing the concentrated cell-seeded microcarrier to cause the formation of a consolidated construct of the desired geometry.

The inventors have cultured chondrocytes on microcarriers for an extended period of time and have found that the cells continue to secrete extracellular matrix and eventually to aggregate and to produce a cartilage-like material. In experiments conducted chondrocytes were cultured and within 30 days the chondrocytes aggregated and produced cartilage like material. These aggregated chondrocytes can per se be cut and shaped for use as a transplant or the chondrocytes can be grown on microcarriers in a mold as described below.

Alternatively cell-microcarrier constructs may be harvested prior to the formation of large aggregates, concentrated to a denser injectable suspension, and injected into the desired anatomic site to form the implant in situ. The suspension of aggregates may contain a soluble component capable of forming a polymer or gel after implantation in order, for example, to secure the solid implant in the site and/or to promote rapid adherence and/or integration of the solid implant to surrounding tissues. Examples of such binding materials are fibrin glues, collagen, combinations of fibrin/collagen, transglutaminase-catalyzed binding systems, hyaluronic acid, calcium alginate gels, chitosan derivatives capable of gelling at body temperature, hydrogels such as polyacrylates, polyvinyl alcohols, polyethylene glycols, or polyethylene imines, polyanhydrides or similar materials with suitable gelling compositions. In situ gelling of these materials may be initiated by thermal, enzymatic or chemical catalysts, pH or ionic strength changes or photoinitiation procedures.

Although, the herein disclosed invention has been characterized as using chondrocytes, it may be embodied using any cells that secrete extracellular matrix components suitable for causing the microcarrier-cell suspension to aggregate in suspension culture, in suitable molding devices, or in situ following injection into a body cavity or tissue. Such cells may also include, for example, osteoblasts, myoblasts, fibroblasts such as those harvested from tendon, ligament, skin, meniscus or disk of the temporomandibular joint, or multi-potent stem cells that are capable of differentiating into matrix-producing cells, including mesenchymal stem cells, pluripotent stem cells from muscle, fat, skin, bone marrow stroma or embryonic stem cells. It is to be understood that the current technology may be extended to other organs such as liver, kidney, pancreas, etc.

DETAILED DESCRIPTION OF THE DRAWINGS

Figure 1:
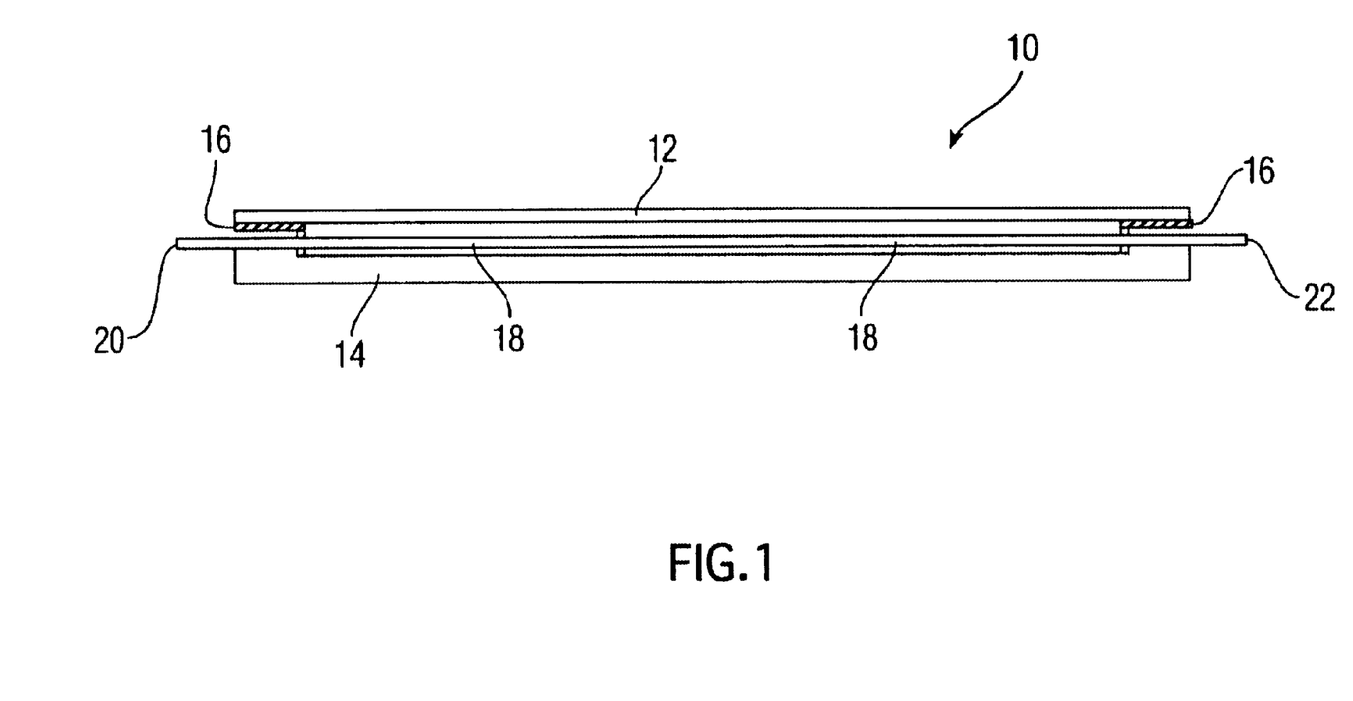
FIG. 1 is a side elevational view of an implant assembly unit (IAU) or culture mold assembly unit with side removed.
Figure 2:
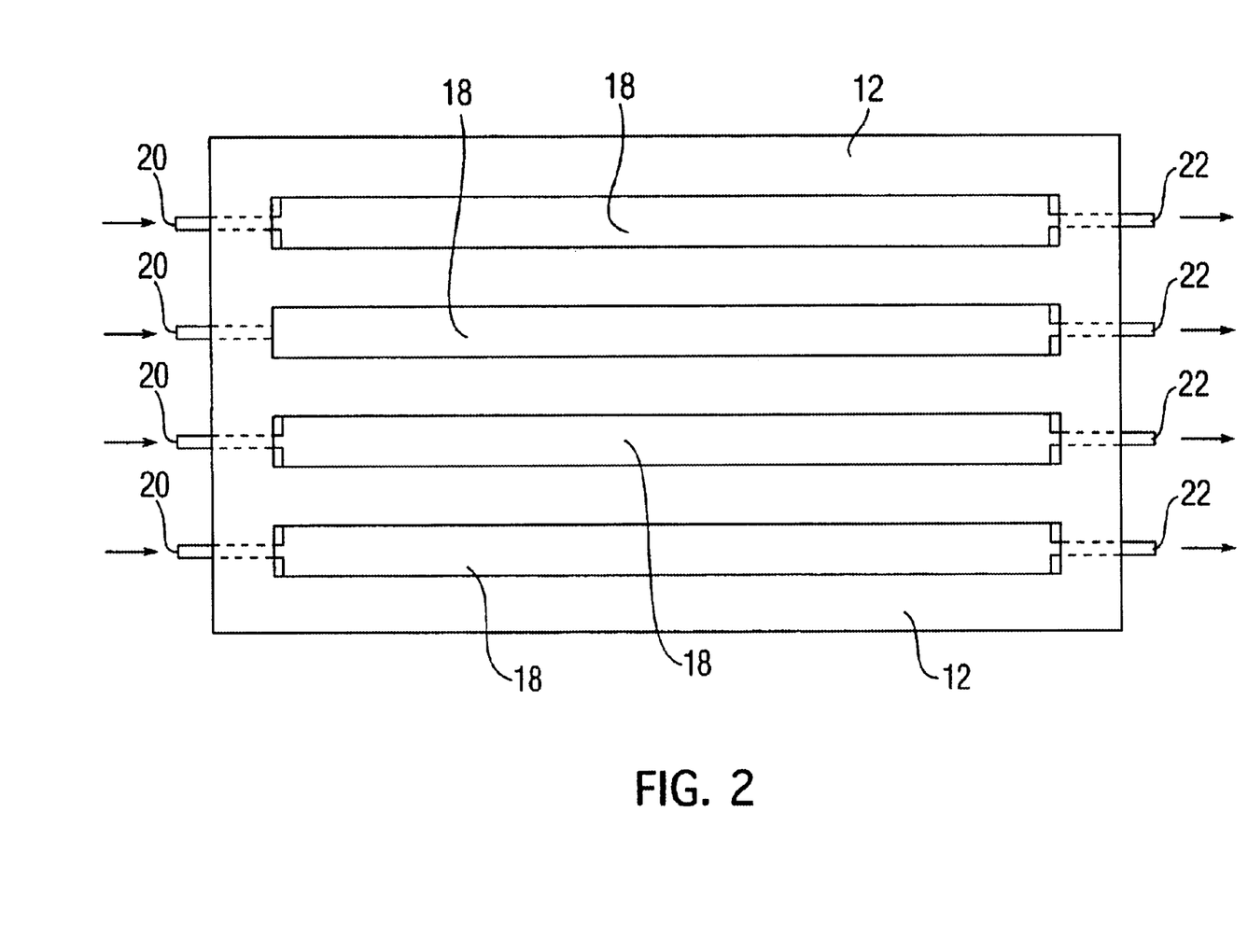
FIG. 2 is a top plan view of the flow culture chamber without the lid.
Figure 3:
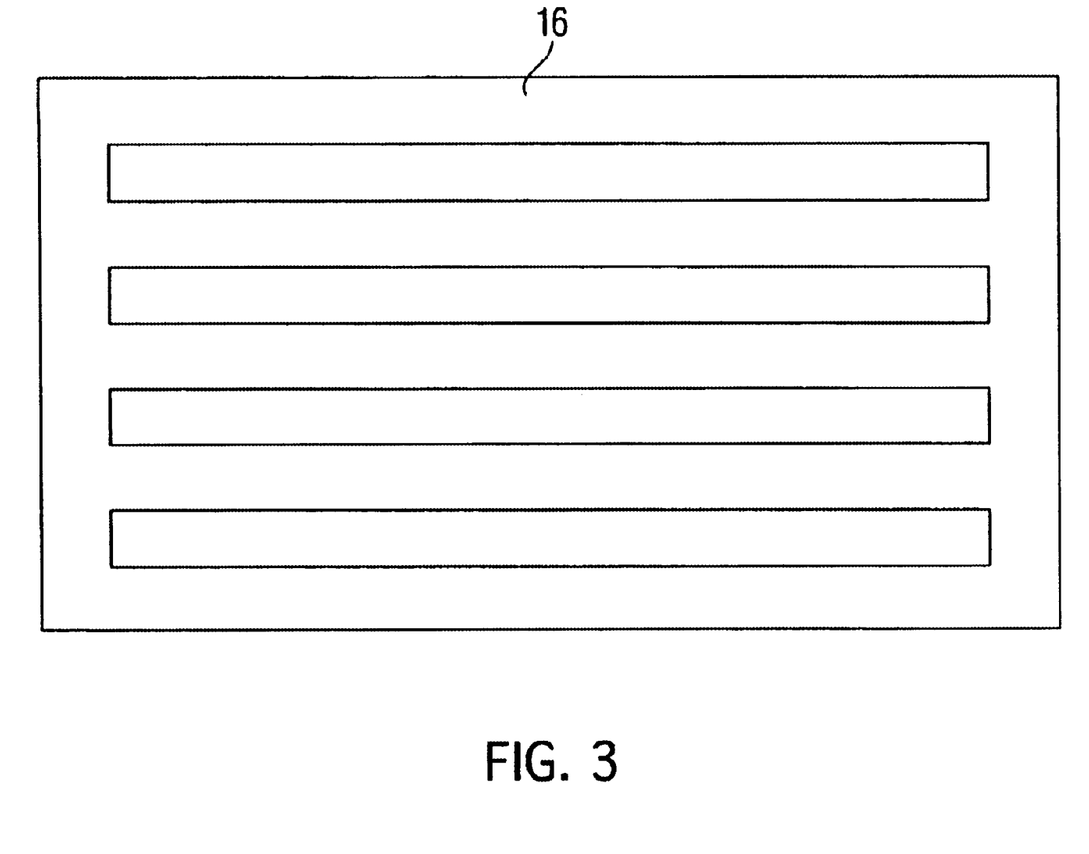
FIG. 3 is the rubber gasket used with the implant assembly unit.
Figure 4:
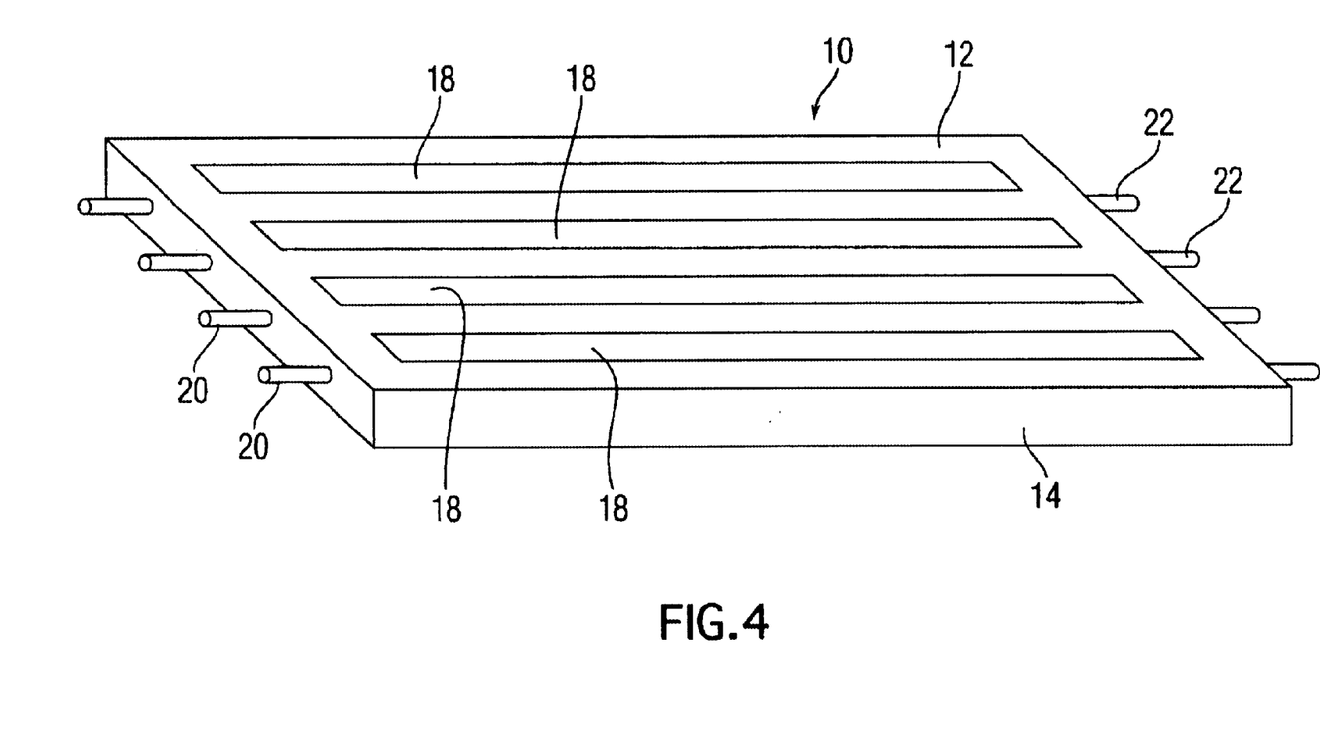
FIG. 4 is a perspective view of the bottom section of the implant assembly unit.

With reference to FIGS. 1–4, one possible embodiment of a culture mold assembly unit 10 has a top lid 12 and a bottom chamber 14 separated by a rubber gasket 16. The bottom chamber 14 has a mold or flow culture chamber 189 or connected at one end with an inlet tube 20 and at the other end at outlet tube 22. The top lid 12 and bottom chamber 14, sealed by the rubber gasket 16 form the flow culture chamber 18 of the culture mold assembly unit 10. The top lid 12 is made of plastic and is 3 mm thick. The rubber gasket 16 is 1 mm thick. The flow culture chamber 18 is 10 mm wide, 140 mm long and 4 mm high. As shown in FIGS. 1 and 4, the mold or flow culture chambers 18 are trough-like. However, the mold or flow culture chambers 18 can be geometrically configured to resemble the tissue which is to be replaced The culture mold assembly unit 10 has its two main sections separated by a rubber gasket 16. More specifically top lid 12 and bottom section housing multiple flow culture chambers 18. As best shown in FIGS. 2 and 4, the flow culture chamber 18 may be multiple.

With reference to FIG. 2, a top plan view of bottom of the chamber. The flow culture chambers 18 are connected to inlet tubes 20 and outlet tubes 22.

With reference to FIG. 3, there is shown a rubber gasket 16 that is used between the top lid 12 and bottom chamber 14 to seal them during culture. The top lid 12, rubber gasket 16 and bottom chamber can be sealed by clamp, bolts through the components or like securing means as readily understood by those skilled in the art.

With reference to FIG. 4, a perspective view of bottom section 14 of the flow culture chamber 18 is shown.

It is pointed out that inlet tube 20 and outlet tube 22 can be attached to a circulating pump arrangement (not shown) to circulate culture fluid required for cell growth.

As shown in the embodiments (FIG. 1-4), the mold flow culture chamber 18 is not shaped to conform to body cavity, however, the flow culture chamber or mold could be shaped to conform to the body cavity into which the molded aggregated cell is to be inserted. Other geometries and designs of the IAU may be anticipated to achieve the desired purpose of shaping the cell-microcarrier aggregates into a specific shape and for culturing the aggregates into a consolidated structure.

Figure 5:
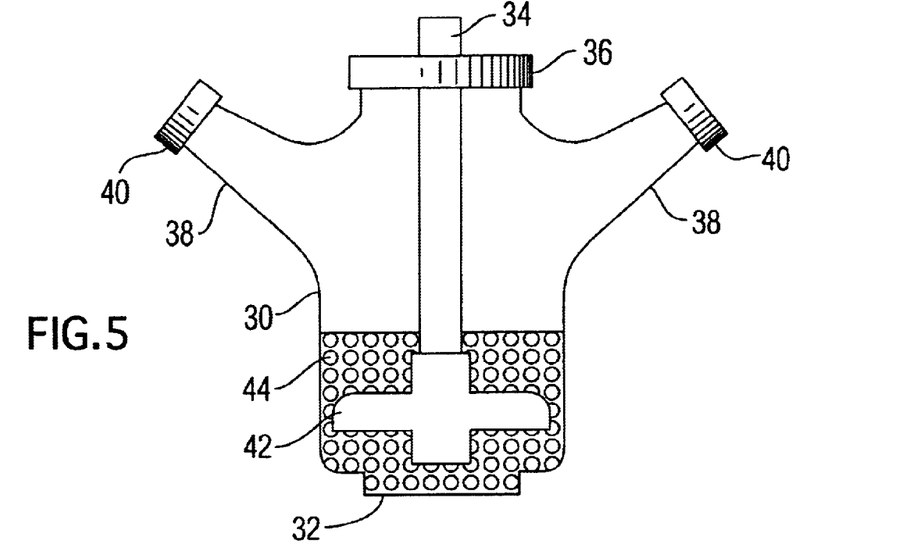
FIG. 5 is a side plan view of a schematic drawing of a spinner culture vessel that incorporates an implant assembly unit into its design.
Figure 6:
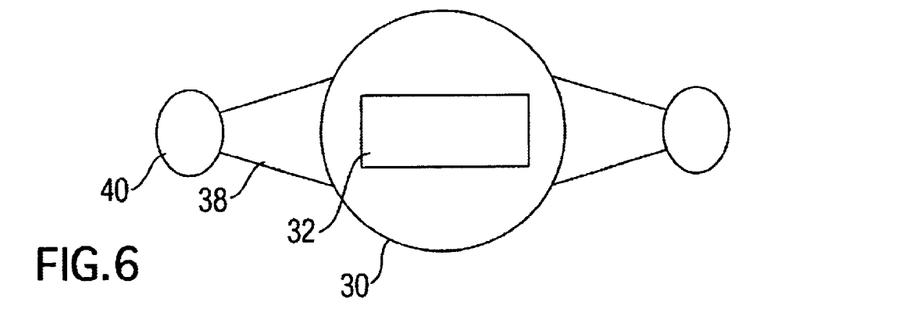
FIG. 6 is a bottom plan view of the spinner culture vessel that incorporates the rectangular implant assembly unit into its design.
Figure 7:
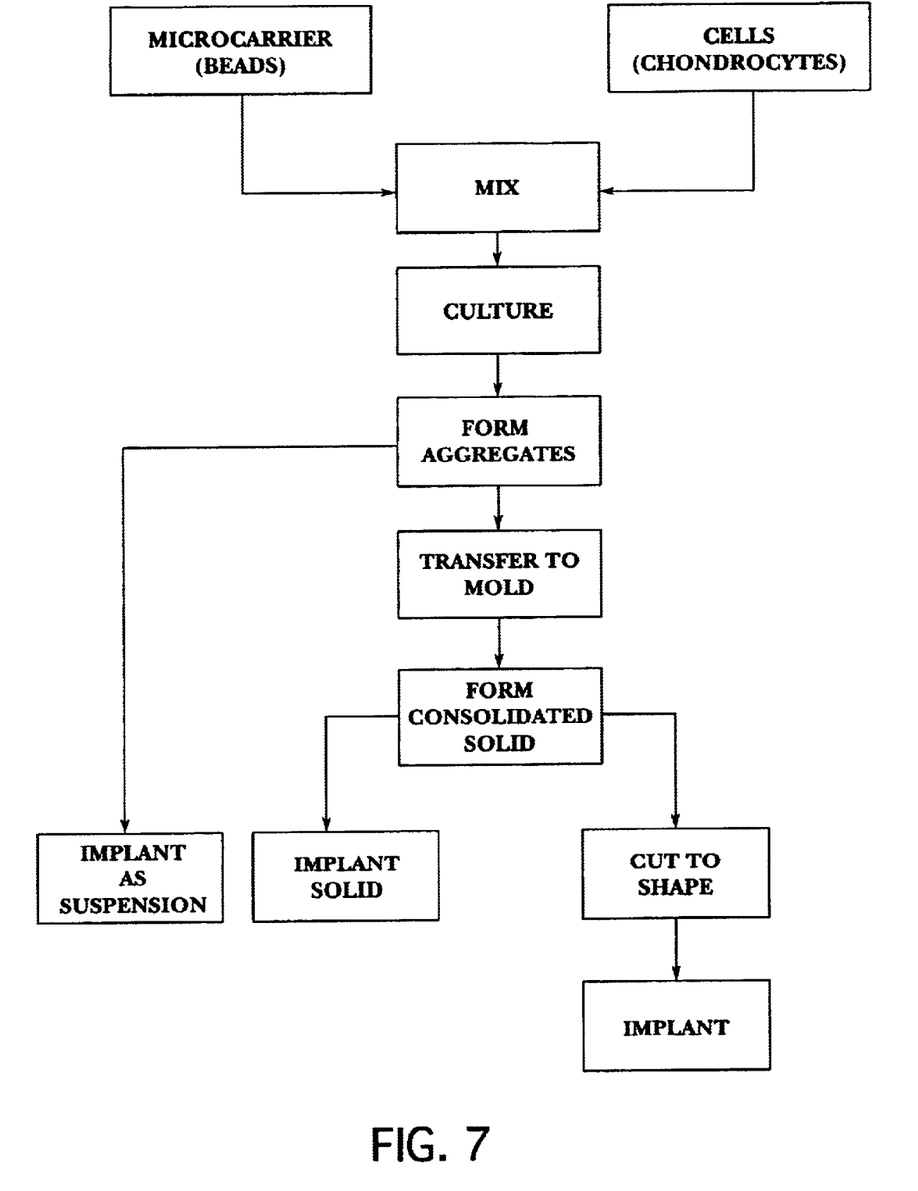
FIG. 7 is a flow chart showing steps for carrying out implantation to repair tissue.

With reference to FIGS. 5 and 6, a second possible embodiment of an implant assembly unit 32 is disclosed in which the IAU is integrated into the design of the spinner culture system 30. The spinner culture system 30 is composed of a cylindrical vessel that is filled to the desired level with cell-microcarrier suspension in cell culture medium 44 and agitated or stirred by means of paddle stirrer 42. The stirrer 42 is affixed to a stirrer shaft 34 that is inserted into vessel through a sealed cap 36 and is rotated mechanically outside of the vessel. Access to the spinner culture system 30 is provided by two or more side-arms 38 that are sealed by screw caps 40.

As illustrated in FIG. 6, the IAU 32 in this example is a rectangular connected compartment of the vessel that extends from the normally flat bottom of the spinner culture vessel 30. When the stirring action of the paddle is stopped by stopping the rotation of the stirrer shaft, cell-microcarrier aggregates that are suspended in the culture medium will sediment under gravity and collect in the IAU 32. After further culturing, the aggregates consolidate in the IAU into a solid material suitable for implantation. Stirring may be subsequently continued after the implant has reached an appropriate state of consolidation.

DETAILED DESCRIPTION OF THE INVENTION

The following steps describe methods for carrying out the disclosed invention.

Step (1). The donor tissue may be autologous or allogeneic, and may be derived from any appropriate tissue, including cartilage, skin, bone, tendon, ligament, meniscus, disk of the temporomandibular joint, bone marrow or marrow stroma, or the like. Cells can be isolated from these tissues by standard mechanical methods (dissecting, mincing), followed by enzymatic methods (collagenase, protease, etc.).

Isolated cells may be of any type of phenotype appropriate for seeding onto microcarrier materials for in vitro cell culture, including, for example: chondrocytes; osteoblasts; fibroblasts derived from skin, tendon, ligament, meniscus, disk or any other connective tissue; stem cells derived from bone marrow stroma, muscle, skin or other stem cell-containing tissue; or combinations of these cells that may be seeded onto the microcarrier.

Step (2). Cells are typically seeded onto the microcarriers at low density ($1–4\times10^3$ cells per $cm^2$), mixing the cells and microcarriers (beads) together for periods sufficient for the cells to adhere to the bead (2–4 hours). Microcarriers (beads) may be in the size range of 100–500 $\mu$m, with the preferred size predominately in the range of 100–300 $\mu$m.

The microcarrier may be inorganic resorbable materials suitable for maintaining seeded cells in culture. Inorganic materials include, for example: calcium phosphates, calcium carbonates, calcium sulfates or combinations of these materials. Organic materials might include, for example: biopolymers such as collagen, gelatin, hyaluronic acid or chemically derived modifications of hyaluronic acid, chitin, chitosan or chitosan derivatives, fibrin, dextran, agarose, or calcium alginate, particles of tissues such as bone or demineralized bone, cartilage, tendon, ligament, fascia, intestinal mucosa or other connective tissues, or chemically modified derivatives of these materials. Organic materials might also include synthetic polymeric materials, including, for example: polylactic acid, polyglycolic acid or copolymers or combinations of the two; polyanhydrides, polyurethanes, polycarbonates, polycaprolactones, hydrogels such as polyacrylates, polyvinyl alcohols, polyethylene glycols, or polyethylene imines, or any other synthetic polymer that can be produced in appropriate bead form. Also contemplated are particles of tissues such as bone or demineralized bone, cartilage, tendon, ligament, fascia, intestinal mucosa or other connective tissues, or chemically modified derivatives of these materials.

In the preferred embodiment, the microcarrier material is biocompatible, and biodegrades or autocatalytically degrades in vivo into biocompatible byproducts. The preferred shaped of the microcarrier is a spherical bead in the range of 50 to 500 $\mu$m, but non-spherical shapes such as cubes, cylinders, plates or irregularly shaped particles may also be employed.

The microcarrier material may also be used as a carrier for bioactive peptides (growth factors, cytokines, integrins, adhesion molecules, etc.), either to be released from the interior of the microcarriers or coated onto the surface of the particles, in order to improve cell adhesion or expansion, expression of phenotypic extracellular matrix, or other characteristics favorable to the production of a suitable implant material.

Step (3). Culture-expansion of the cells can be conducted in stirred or rotating vessels that are normally mixed sufficiently to suspend the cell-microcarrier combination and to provide uniform nutrient and supply oxygen to all of the cells.

Steps (4) and (5). Concentration of the culture-expanded cell-microcarrier material can be achieved by centrifugation, sedimentation, filtration or equivalent methods. In a preferred embodiment, the concentration is achieved in the vessel implant assembly unit, IAU, (10) in which the final implant product is to be cultured and without an intermediate process step in which the cell-microcarrier combination is removed from the IAU.

This method may provide for a subsequent process step wherein the cell-microcarrier aggregates, or consolidated implants prepared therefrom by further culturing in a mold, may be cryopreserved by standard methods in order maintain cell viability and aggregate structure for future implantation or analysis.

In the production of an injectable formulation, cell-microcarrier aggregates may be implanted without any additional material to bind the aggregates together after implantation. Alternatively, a material capable of polymerizing or gelling after implantation may be mixed with the aggregate suspension prior to implantation in order to improve the fixation and localization of the aggregates after implantation, to stimulate more rapid consolidation of the aggregates in vivo, or to promote more rapid integration of the aggregates into the surrounding tissue. Examples of such binding materials are fibrin glues, collagen, combinations of fibrin/collagen, transglutaminase-catalyzed binding systems hyaluronic acid, calcium alginate gels, chitosan derivatives capable of gelling at body temperature, hydrogels such as poly acrylates, poly vinyl alcohols, poly ethylene glycols, or poly ethylene imines, or similar materials with suitable gelling compositions. In situ gelling of these materials may be initiated by thermal, enzymatic or chemical catalysts, pH or ionic strength changes or photo-initiation procedures.

Advantages. This method results in the formation of an in-vitro-cultured implant without the need for a preformed scaffold onto which the cells are initially seeded. The method provides for two formulation strategies for implantation of cell-microcarrier aggregates, either as an injectable dispersion of aggregates or as a solid stucture of consolidated aggregates prepared by further culturing of aggregates in a mold device. By this latter method, the final shape of the solid implant is determined by the geometry of the mold in which the consolidation of the cell-containing microcarrier aggregates is conducted. Because no separation of the culture-expanded cells from the microcarriers is required in the spinner culture vessel, the method can be conducted in a "closed" system following introduction of the isolated donor cells.

EXAMPLE 1

This example illustrates that chondrocytes propagated in spinner culture on biopolymer beads eventually aggregate into cartilage-like masses.

In this experiment, the inventors tested the hypothesis that nasal chondrocytes propagated in microcarrier spinner culture would proliferate and produce extracellular matrix components similar to that produced by articular chondrocytes. Cartilage was obtained from five patients during nasal septum reconstruction. Chondrocytes isolated by collagenase digestion were directly seeded at $4 \times 10^3$ cells/cm$^2$ onto Cellagen microcarriers (100–400 cm$^2$, derived from bovine corium, (ICN, Cleveland, Ohio)) or in monolayer culture. Monolayer and microcarrier spinner cultures were incubated at 37° C., 5% $CO_2$ for fourteen days. Chondrocytes were harvested and cell samples enumerated in trypan blue vital dye. To analyze for proteoglycans production, cells were pulsed for 60 hours with 50 $\mu$Ci/ml, $^{35}SO_4$. The proteoglycans were extracted using 4M guanidium HCl for 24 hours at 4° C. and radiolabeled incorporation was determined by liquid scintillation counting. Aliquots were electrophoresed on 0.6% agrose-1.25 polyacrylamide gels and then autoradiographed. The Dc protein assay from BioRad was used to assess protein concentration in the cell-associated fractions (CAF). The protein concentration in the CAF was used to normalize the total CPM in each fraction. Replicates of the cells were frozen for subsequent RNA isolation. Gene markers were determined using RT-PCR.

Chondrocytes isolated from nasal cartilage proliferated in microcarrier spinner culture within two weeks. Cell numbers increased up to 17-fold and the microcarriers seeded with nasal chondrocytes cultured to about a month began to aggregate. A cartilage-like material was produced within thirty days. Chondrocytes expressed collagen type II and aggrecan but not collagen type I. Propagation of chondrocytes from this cartilage site in spinner culture maintained the expression of collagen type II while decreasing the expression of collagen type I.

This example demonstrates that nasal chondrocytes multiply in Cellagen-microcarrier spinner culture. Thus, chondrocytes retrieved from a non-articulating cartilaginous site are able to maintain features of their original phenotype. After 30 days in culture, cell-microcarrier constructs had aggregated to form consolidated structures with cartilage-like properties. These aggregated materials would be suitable for implantation, but the properties of the implant would be improved if the shape of the aggregate mass were better controlled to provide a shape more anatomically correct or a more surgically useful material. The implant assembly unit of this invention fulfills this function.

EXAMPLE 2

Steps (1) and (2) of Example 1 are performed by the same procedures.

Step (3). The cell-seeded microcarriers are maintained in spinner culture at 60 rpm, 37° C., 5% $CO_2$ for 14 to 21 days to allow visible aggregation to take place in enriched medium (Dulbecco essential media containing NCTC-109, OPI (oxaloacetate, pyruvate, insulin), 1-glutamine, gentamycin, and fetal calf serum). The cell-microcarrier aggregates are subsequently centrifuged at 200 g for 15 minutes and 4° C. The supernatant fluid is removed and the aggregates are resuspended in the same enriched media described above.

Step (4). The resuspended aggregates are next transferred by pipetting into the "implant assembly unit (IAU)," as shown in 10. The IAU 10 is siliconized and sterilized before use. The aggregate suspension is transferred into the individualized channel or trough 18 of the "implant assembly unit". The top lid 12 is then positioned over bottom chamber 14, separated by the rubber gasket 16. The top lid 12, rubber gasket 16 and bottom chamber 14 are joined by screws (not shown), but other joining means such as clamps could be used. Fresh media is delivered to fill the channel by infusing the required volume of media via the inlet tube or port 20. Once the individual channel or channels 18 are filled, the IAU is mounted on a platform stoker (not shown). The IAU and the platform rocker are then placed in a 37° C., 5% $CO_2$ incubator.

Step (5). Fresh culture media from a reservoir container is then delivered in a continuous flow to the inlet tube 12 from a peristaltic pump (not shown) to achieve a 1–10 dynes/cm$^2$ in the individual IAU channel or mold 18 containing the cell microcarrier aggregates. Effluent spent media is allowed to exit through the opposite end of the channel 18 via an outlet tube 22 and is collected in a disposal media collector vessel. The platform shaker is turned on at the optimum cycle to insure that the aggregates remain in suspension throughout the IAU channel, and are subject to continuous agitation. The cell-microcarrier aggregates are incubated from one to five weeks until the newly developed construct consisting of extracellular matrix produced by the cells fills the individual mold. The IAU is then removed from the platform. The lid is unscrewed and the newly formed construct is removed from the channel. The construct is ready to use or may be cut further as needed to fit the tissue defect.

At times, it may be advisable to cultivate the chondrocytes for up to 60 days to obtain optimum adherence and growth.

The invention is also directed to a method of replacing a tissue or body part or filling a void in head and neck area comprising the steps of obtaining a non-diseased cell sample from the respective patient's head and neck area, rapidly growing additional cells in a bioreactor and within a predetermined mold or culture chamber which is the mirror image of the patient's tissue, body part or void, such that a molded tissue or body part is produced, and surgically implanting the molded tissue or body part as a replacement in the patient's head and neck area, such that the molded tissue or body part regenerates therein and may thereby integrate with the adjacent tissues in the head and neck area of the respective patient. The method also involves obtaining the nasal area and the cells can be chondrocytes. The method can include a scaffold made from a biodegradable microcarrier material for supporting the molded tissue or body part. In a more general embodiment of the invention, cells may be obtained from any anatomic location of the patient to receive the implant or from another donor human, and the resulting material produced by the method may be implanted at any location requiring the implant.

EXAMPLE 3

Steps (1) and (2) of Example 1 are performed by the same procedures.

Step (3). The cell-seeded microcarriers are maintained in spinner culture at 60 rpm, 37° C, 5% $CO_2$ for 14 to 21 days to allow visible secretion of extracellular matrix to take place in enriched medium (Dulbecco essential media containing NCTC-109, OPI (oxaloacetate, pyruvate, insulin), 1-glutamine, gentamycin, and fetal calf serum). The cell-microcarrier aggregates are subsequently centrifuged at 200 g for 15 minutes and 4° C. The supernatant fluid is removed and the aggregates are resuspended in a fluid medium, such as isotonic saline, phosphate buffered saline solution or Hank's balanced salt solution, suitable for injection into the body.

Step (4). The resuspended aggregates are next transferred to a syringe or other suitable implantation device whereby the suspension is implanted directly into the anatomic site or cavity requiring the cartilage implant. During the next 14–28 days, or after a suitable period depending on the site, the cells continue to secrete extracellular matrix, thereby consolidating the cell-microcarrier suspension into a solid cartilage-like mass.

EXAMPLE 4

Steps (1) and (2) are conducted as described in Example 2.

Step (3). The cell-seeded microcarriers are maintained in spinner culture at 60 rpm, 37° C., 5% $CO_2$ for 14 to 21 days to allow visible secretion of extracellular matrix to take place in enriched medium (Dulbecco essential media containing NCTC-109, OPI (oxaloacetate, pyruvate, insulin), 1-glutamine, gentamycin, and fetal calf serum).

Step (4). The stirrer is stopped and the cell-microcarrier suspension is allowed to concentrate by sedimentation in the implant assembly compartment.

Step (5). Supernatant medium is removed from the system by pumping or other transfer method and fresh medium is added. Culturing is continued for one to five weeks, or until a consolidated product is formed having the shape of the implant assembly compartment.

EXAMPLE 5

Steps (1) and (2) of Example 1 are performed by the same procedures.

Step (3). The cell-seeded microcarriers are maintained in spinner culture at 60 rpm, 37° C., 5% $CO_2$ for 14 to 21 days to allow visible secretion of extracellular matrix to take place in enriched medium (Dulbecco essential media containing NCTC-109, OPI (oxaloacetate, pyruvate, insulin), 1-glutamine, gentamycin, and fetal calf serum). The cell-microcarrier aggregates are subsequently centrifuged at 200 g for 15 minutes and 4° C. The supernatant fluid is removed and the aggregates are resuspended in a fluid medium, such as isotonic saline, phosphate buffered saline solution or Hank's balanced salt solution, suitable for injection into the body. In this example, fibrinogen solution is added in concentration sufficient to form a gel in vivo, and thrombin is added in sufficient concentration to cause the formation of a fibrin gel in 5–10 minutes in vivo.

Step (4). The resuspended aggregates are next transferred to a syringe or other suitable implantation device whereby the suspension is implanted directly into the anatomic site or cavity requiring the cartilage implant. Rapid gelation of the fibrinogen/thrombin system promotes a fibrin gel in situ that stabilizes the localization of the injected aggregates, yet permits continued extracellular matrix components. During the next 14–28 days, or after a suitable period depending on the site and the rate degradation of the fibrin gel, the cells continue to secrete extracellular matrix, thereby consolidating the cell-microcarrier suspension into a solid cartilage-like mass.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. A method of preparing and then implanting cells comprising the steps of culturing said cells to grow and proliferate on microcarrier particles in a stirred bioreactor under normal gravity conditions for an extended period of time to secrete an extracellular matrix thereby producing a cell-microcarrier particle aggregate and then implanting said cell-microcarrier particle aggregate into a patient to replace and repair damaged or diseased tissue.

2. The method of claim 1 wherein the cells secrete extracellular matrix to create a tissue-like implant.

3. The method of claim 1 wherein the cell-microcarrier aggregates are suspended in a medium suitable for injection for use in repairing or reconstructing missing or diseased tissues, comprising the steps of, (1) isolating the cells to be implanted from donor tissue; (2) seeding the cells onto a resorbable microcarrier; (3) culturing the cells on microcarriers to achieve an expansion in the number of cells and the secretion of extracellular matrix; (4) transferring cell-containing microcarriers to a medium suitable for injection; and implanting the cell-microcarrier aggregates by injection.

4. The method of claim 3 wherein the cell-microcarrier aggregates are implanted into a cavity or an anatomic site requiring repair or replacement of missing or diseased tissue.

5. The method of claim 3 wherein the cells are chondrocytes.

6. The method of claim 3 wherein the cells are extracellular matrix producing cells selected from chondrocytes; osteoblasts; fibroblasts derived from skin, tendon, ligament, meniscus, disk or any other connective tissue; stem cells derived from skin, tendon, ligament, meniscus, disk, or any other connective tissue; stem cells derived from bone marrow stroma, muscle, skin or other stem cell-containing tissue; embryonic stem cells; or combinations of these cells that may be seeded onto the microcarrier.

7. The method of claim 3 wherein the microcarrier is a biodegradable material.

8. The method of claim 3 wherein the microcarrier is selected from inorganic materials selected from the group of calcium phosphates, calcium carbonates, calcium sulfates or combinations of these materials; organic materials selected from the group of biopolymers, collagen, gelatin, hyaluronic acid, chemically derived modifications of hyaluronic acid, chitin, chitosan, chitosan derivatives, fibrin, dextran, agarose, or calcium alginate, or synthetic polymeric materials, polylactic acid, polyglycolic acid or copolymers or combinations of the two, polyurethanes, polycarbonates, polycaprolactones, hydrogels such as poly acrylates, poly vinyl alcohols, poly ethylene glycols, or poly ethylene imines; or particles of tissues such as bone or demineralized bone, cartilage, tendon, ligament, fascia, intestinal mucosa or other connective tissues, or chemically modified derivatives of these materials.

9. The method of claim 3 wherein the fluid medium suitable for injection is selected from isotonic saline for injection, phosphate buffered saline, or Hank's balanced salt solution.

10. The method claim 3 wherein the fluid medium suitable for injection contains a material capable of polymerizing or gelling after implantation.

11. The method of claim 6 wherein the material is selected from fibrin glues, collagen, combinations of fibrin/collagen, transglutaminase-catalyzed binding systems, hyaluronic acid, calcium alginate gels, chitosan derivatives capable of gelling at body temperature, hydrogels such as polyacrylates, polyvinyl alcohols, polyethylene glycols, or polyethylene imines, or similar materials with suitable gelling compositions.

12. The method of claim 10 where in the in situ gelling of these materials is initiated by thermal, enzymatic or chemical catalysts, pH or ionic strength changes or photo-initiation procedures.

13. The method of claim 1 wherein the cell-microcarrier aggregates are further cultured inside a mold which has been shaped to configure the geometry of the area of the body receiving the cells for implantation.

14. The method of claim 13 wherein the mold is shaped to produce a form that can be or modified to a desired shape at the time of implantation.

15. The method of claim 13 wherein the cell-microcarrier aggregates are consolidated into an implantable structure for repair or replacement of missing or diseased tissue.

16. The method of claim 13 wherein the cell-microcarrier aggregates are implanted into a cavity or an anatomic site requiring repair or replacement of missing or diseased tissue.

17. The method of claim 1 wherein the cells are chondrocytes.

18. The method of claim 1 wherein the cells are extracellular matrix producing cells selected from chondrocytes; osteoblasts; fibroblasts derived from skin, tendon, ligament, meniscus, disk or any other connective tissue; stem cells derived from skin, tendon, ligament, meniscus, disk or any other connective tissue; stem cells derived from bone marrow stroma, muscle, skin or other stem cell-containing tissue; embryonic stem cells; or combinations of these cells that may be seeded onto the microcarrier.

19. The method of claim 1 wherein the microcarrier is a biodegradable material.

20. The method of claim 1 wherein the microcarrier is selected from inorganic materials such as calcium phosphates, calcium carbonates, calcium sulfates or combinations of these materials; organic materials including biopolymers selected from the group consisting of collagen, gelatin, hyaluronic acid or chemically derived modifications of hyaluronic acid, chitin, chitosan, chitosan derivatives, fibrin, dextran, agarose, calcium alginate, synthetic polymeric materials selected from the group consisting of polylactic acid, polyglycolic acid or copolymers or combinations of the two, polyurethanes, polycarbonates, polycaprolactones, polyanhydrides, hydrogels selected from the group consisting of polyacrylates, polyvinyl alcohols, polyethylene glycols, polyethylene imines, or particles of tissue such as bone or demineralized bone, cartilage, tendon, ligament, fascia, intestinal mucosa or other connective tissues, or chemically modified derivatives of these materials.

21. The method of claim 1 wherein the cell-microcarrier aggregate is prepared by culturing said cells to grow and proliferate on microcarrier particles for an extended period of time of from about seven to sixty days thereby producing a cell-microcarrier particle aggregate useful for implantation.

22. The method of claim 21 wherein the cells are chondrocytes.

23. The method of claim 21 wherein the cells are selected from chondrocytes; osteoblasts; fibroblasts derived from skin, tendon, ligament, meniscus, disk or any other connective tissue; stem cells derived from bone marrow stroma, muscle, skin or other stem cell-containing tissue; embryonic stem cells; or combinations of these cells that may be seeded onto the microcarrier.

24. The method of claim 1 wherein the growth and proliferation is over an extended period of time of about five weeks.

25. The method of claim 1 wherein the growth and proliferation is over an extended period of time of about 28 days.

26. The method of claim 1 wherein the growth and proliferation is over an extended period of time of about 30 days.

27. The method of claim 1 wherein the growth and proliferation is over an extended period of time of about 14–28 days.

28. The method of claim 1 wherein the growth and proliferation is over an extended period of time of about 60 days.

29. A method of preparing and then implanting chondrocytes comprising the steps of culturing said chondrocytes on microcarriers in an implant assembly unit for a period of time under normal gravity conditions by which said chondrocytes secrete and extracellular matrix and aggregate and thus can be shaped or cut to conform to the body area which will receive said chondrocytes and then implanting said chondrocytes in a patient to replace and repair damaged or diseased tissue.

30. The method of claim 29 wherein culturing is carried out in an implant assembly unit.

31. A method of claim 29 wherein the cells are chondrocytes.

32. The method of claim 29 wherein the cells are selected from chondrocytes; osteoblasts; fibroblasts derived from skin, tendon, ligament, meniscus, disk or any other connective tissue; stem cells derived from bone marrow stroma, muscle, skin or other stem cell-containing tissue; embryonic stem cells; or combinations of these cells that may be seeded onto the microcarrier.

33. The method of claim 31 wherein the culturing of said cells takes place over one to five weeks.

34. The method of claim 31 wherein the cells are seeded onto the microcarrier at a density of 1 to $4\times10^3$ cells/cm$^2$.

* * * * *